(12) United States Patent
Kale et al.

(10) Patent No.: US 11,490,849 B2
(45) Date of Patent: Nov. 8, 2022

(54) SYSTEM AND METHOD OF MARKING CARDIAC TIME INTERVALS FROM THE HEART VALVE SIGNALS

(71) Applicant: AventuSoft, LLC, Boca Raton, FL (US)

(72) Inventors: Kaustubh Kale, Royal Palm Beach, FL (US); Arash Andalib, Delray Beach, FL (US)

(73) Assignee: Aventusoft, LLC, Boca Raton, FL (US)

(*) Notice: Subject to any disclaimer, the term of this patent is extended or adjusted under 35 U.S.C. 154(b) by 101 days.

(21) Appl. No.: 16/741,740

(22) Filed: Jan. 13, 2020

(65) Prior Publication Data

US 2020/0170527 A1 Jun. 4, 2020

Related U.S. Application Data

(63) Continuation-in-part of application No. 15/397,138, filed on Jan. 3, 2017, now Pat. No. 10,531,839.

(51) Int. Cl.
| | |
|---|---|
| *A61B 5/339* | (2021.01) |
| *A61B 5/00* | (2006.01) |
| *A61B 8/08* | (2006.01) |
| *G06K 9/62* | (2022.01) |
| *G06N 20/10* | (2019.01) |
| *A61B 5/332* | (2021.01) |

(52) U.S. Cl.
CPC .............. *A61B 5/339* (2021.01); *A61B 5/332* (2021.01); *A61B 5/7225* (2013.01); *A61B 5/7282* (2013.01); *A61B 8/0883* (2013.01); *G06K 9/6247* (2013.01); *G06N 20/10* (2019.01); *A61B 2562/0219* (2013.01)

(58) Field of Classification Search
CPC . A61B 5/339; A61B 5/332; A61B 2562/0219; G06K 9/6247
See application file for complete search history.

(56) References Cited

U.S. PATENT DOCUMENTS

| | | | |
|---|---|---|---|
| 10,531,839 B2* | 1/2020 | Kale | A61B 5/364 |
| 2011/0263994 A1* | 10/2011 | Burns | A61B 5/339 600/509 |
| 2014/0296726 A1* | 10/2014 | Brockway | H03H 17/0248 600/514 |
| 2017/0188866 A1* | 7/2017 | Kale | G06N 3/0454 |
| 2021/0127983 A1* | 5/2021 | Parchani | A61B 5/7264 |

* cited by examiner

Primary Examiner — George R Evanisko
(74) Attorney, Agent, or Firm — Pablo Meles

(57) ABSTRACT

A system for marking cardiac time intervals from heart valve signals includes a non-invasive sensor unit for capturing electrical signals and composite vibration objects, a memory containing computer instructions, and one or more processors coupled to the memory. The one or more processors causes the one or more processors to perform operations including separating a plurality of individual heart vibration events into heart valve signals from the composite vibration objects, and marking cardiac time interval from the heart valve signals by detecting individual heartbeats using at least one or more of a PCA algorithm or deep learning.

16 Claims, 10 Drawing Sheets

110

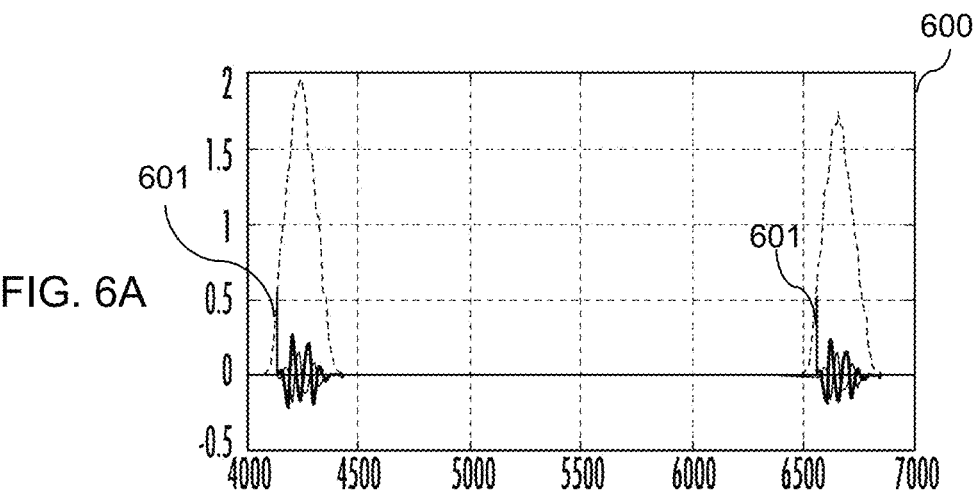

FIG. 6A

PARAMETERS: CUMULATIVE ENERGY THRESHOLD $\epsilon$
INPUTS: SOURCE SIGNAL $Y_i$
OUTPUTS: TIME OF EVENT VECTOR t 1: COMPUTE $\Delta_i$ FROM $Y_i$
2: COMPUTER THE LEADING RIGHT SINGULAR VECTORS $u_1$ AND $u_2$
3: OBTAIN THE SCORE VECTORS $s_1$ AND $s_2$
4: CALCULATE ENERGY ENVELOPE s AS SHOWN IN (5)
5: FIND END POINTS OF ENVOLPE $t_{str}$ AND $t_{end}$
6: CALCULATE CUMULATIVE ENERGY BETWEEN $(t_{str})_i$ AND $(t_{end})_i$
7: ASSIGN TIME STAMP
$$(t)_i = (t_{str})_i + \min(\{t : (\operatorname{cum}(s, (t_{str})_i, (t_{end})_i))_t > \epsilon\})$$

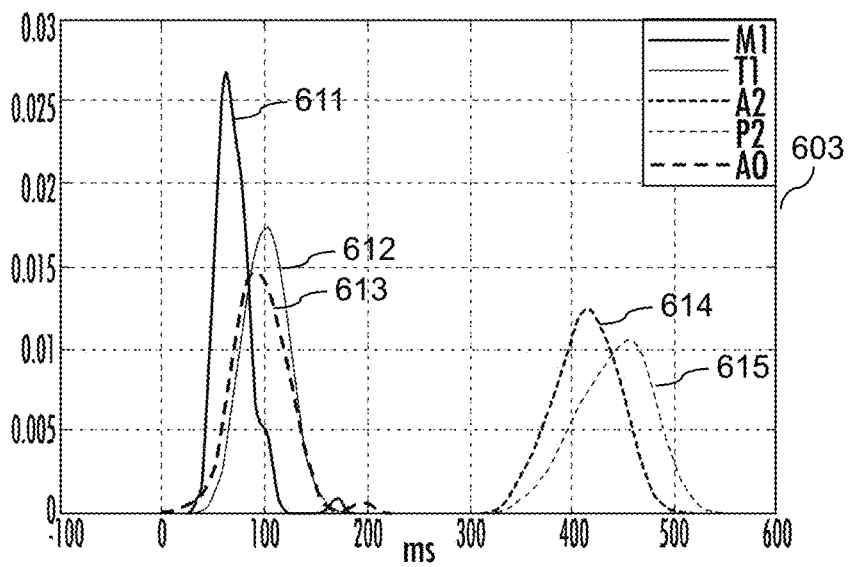

FIG. 6C

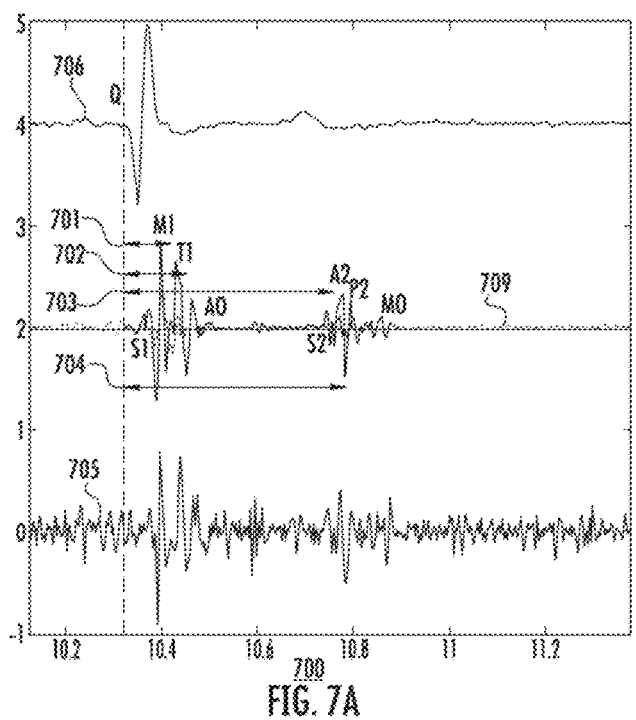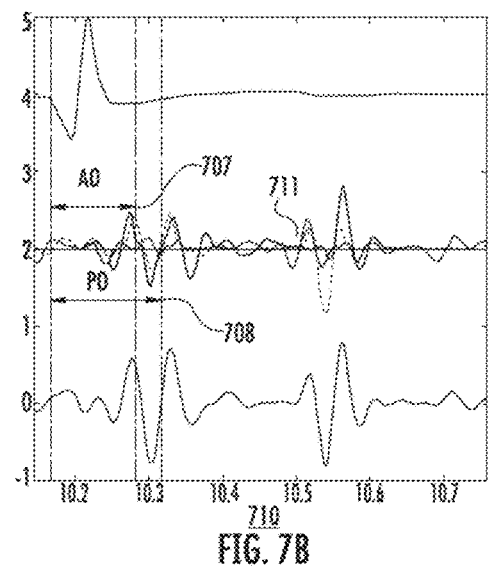
FIG. 7A
FIG. 7B

800

810

820

900

1000

1100

SYSTEM AND METHOD OF MARKING CARDIAC TIME INTERVALS FROM THE HEART VALVE SIGNALS

CROSS REFERENCE TO RELATED APPLICATIONS

This Application is a Continuation-in-Part of and claims priority through U.S. patent application Ser. No. 15/397,138 filed on Jan. 3, 2017 which further claims the priority benefit of Provisional Application Nos. 62/274,766, 62/274,761, 62/274,763, 62/274,765, and 62/274,770 each of which were filed on Jan. 4, 2016, the entire disclosure of each are incorporated herein by reference.

FIELD

The embodiments herein relate generally to cardiopulmonary health monitoring and more particularly to analysis software combined with transducers to capture multi-channel vibration signals along with an electrocardiogram signal for the measurement of heart functions.

BACKGROUND

Heart disease is the leading cause of death accounting for more than one-third (33.6%) of all U.S. deaths. Overall cardiac health can be significantly improved by proper triage. Low invasive and non-invasive ultrasound techniques (e.g. echocardiogram) are standard procedures, but the requirement of expensive devices and skilled operators limit their applicability. The following are the various types of heart disease that can be diagnosed and treated using the separated signal, namely, Coronary artery disease, Heart murmurs and valve abnormalities, Heart failure, Heart rhythm abnormalities (arrhythmias), Vascular disease, congenital heart disease, Cardiac resynchronization and Risk factor modification. A physician can work with patients to perform a comprehensive evaluation and design a personalized plan of care aimed at keeping them healthy.

The cardio pulmonary system which consists of the respiratory components, snoring components, and cardiac components, creates vibrations during each cardiac cycle. The vibrations are the result of the lung sounds, heart sounds, acceleration and deceleration of blood due to abrupt mechanical opening and closing of the heart valves during the cardiac cycle.

SUMMARY

The exemplary embodiments herein provide a method and system of marking cardiac time intervals from the source separated heart valve signals from the composite cardiac vibration objects. In some embodiments, data is obtained using a tri-axial accelerometer or multiple tri-axial accelerometers placed on different points of torso. The present technology pertains in general to technology for assessment of cardiac contractility in a subject from the source separated signals from recorded precordial acceleration signals. The embodiments herein can use machine learning, Principal Component Analysis (PCA), Singular Value Decomposition (SVD), k nearest neighbors, Linear LDA, Quadratic LDA, Linear SVM, or rbf SVM or others.

Examples of cardiac vibration objects are the first sound, the second sound, the third sound, the fourth sound, ejection sounds, opening sounds, murmurs, heart wall motions, coronary artery sounds, and valve sounds of the Mitral valve opening and closing, Aortic valve opening and closing, Pulmonary valve opening and closing, Tricuspid valve opening and closing. Examples of the pulmonary vibration objects are the respiratory lung sounds, breathing sounds, tracheobronchial sounds, vesicular sounds, Broncho vesicular sounds, snoring sounds. A portion of the energy produced by these vibrations lies in the infra-sound range, which falls in the inaudible and low sensitivity human hearing range. A portion of the energy produced by these vibrations falls in the audible hearing range. For example, the vibration objects from the Mitral, Tricuspid, Aortic, and Pulmonary valve openings fall in a lower range of vibrations such as 0 to 60 Hertz, whereas vibration objects from the Mitral, Tricuspid, Aortic, and Pulmonary valve closings fall in a higher range of vibrations such as 50 to 150 Hertz. Accelerometer transducers placed on the chest capture these vibrations from both these ranges.

Source separation analysis extract individual vibration objects from the composite vibration signal captured on the surface (of the torso or elsewhere). The individual vibration signals are identified to be from the mitral valve, aortic valve, tricuspid valve, and the pulmonary valve during individual heart beats. Along with separating breathing sounds, and heart wall motion. The identified valve signals are marked to indicate their start and end of the event with respect to the start of the EKG to provide the cardiac time intervals as described in the embodiments herein. These events correspond to the opening and closing of each valve. Further note that the techniques and methods herein are not limited to acoustic, electrical or vibrational data as might be used in some stethoscopes, but can also be applied to other forms of monitoring such as echo imaging or sonograms, magnetic resonance imaging (MRI), computed tomography (CT) scanning, positron emission tomography (PET) scanning, and monitoring using various forms of catheterization. The techniques and methods herein are primarily applicable to monitoring of heart valve events, but can be alternatively applied to other types of involuntary biological signaling emanating from the brain, intrauterine, pre-natal contractions, or elsewhere within both humans and other species.

DESCRIPTION OF THE DRAWINGS

FIGS. 6A, 6B, and 6C illustrate a method and a cardiac time interval measurement in accordance with one embodiment;

FIGS. 7A and 7B illustrate the marking of vibration objects or each valve into individual streams in accordance with one embodiment;

DETAILED DESCRIPTION

Figure 1A:
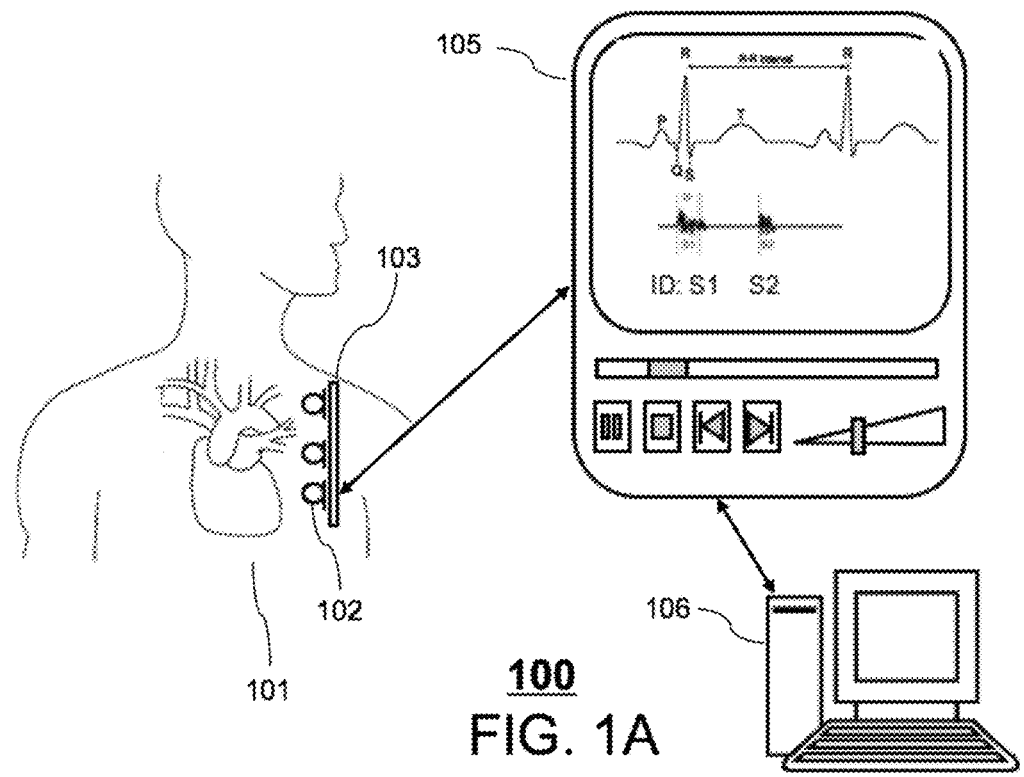
FIG. 1A illustrates a system for the extraction, identification, marking and display of the heart valve signals in accordance with one embodiment.

The exemplary embodiments may be further understood with reference to the following description and the appended drawings, wherein like elements are referred to with the same reference numerals. The exemplary embodiments describe a system and method of marking the cardiac time intervals and display of the heart valve signals. Specifically, psychoacoustics are considered in identifying the separated cardiac vibration signals captured through the transducers. The system, the psychoacoustics, and a related method will be discussed in further detail below.

The exemplary embodiments provide a novel approach for small, portable, robust, fast and configurable source separation based software with transducer hardware. The use of a vibration signal pattern and novel psychoacoustics help bypass conventional issues faced by linear time invariant systems. Clinical indices of myocardial contractility can be categorized as follows based on pressure measurements (such as dP/dtmax), volume and dimension (such as stroke volume and ejection fraction) and systolic time intervals (such as pre-ejection period, left ventricular ejection time and isovolumic contraction time). dP/dtmax is the gold standard of measurement of myocardial contractility. Some of the cardiac time intervals can include Left Ventricular Systolic Time (LVST), Left Ventricular Diastolic Time (LVDT), Pre-atrial Diastolic Filling Time (PADT), Accelerated Atrial Filling Time (AAFT), QS1 (Electromechanical activation time), QS2, Pre-Ejection Period (PEP), Right Ventricular Systolic Time (RVST), Left Atrial Systolic Time (LAST), Right Atrial Systolic Time (RAST), Right Ventricular Ejection Fraction (RVEF), Right Ventricular Diastolic Time (RVDT), Left Atrial Diastolic Time (LADT), Right Atrial Diastolic Time (RADT), Systolic Time Interval (PEP/LVST).

Figure 1B:
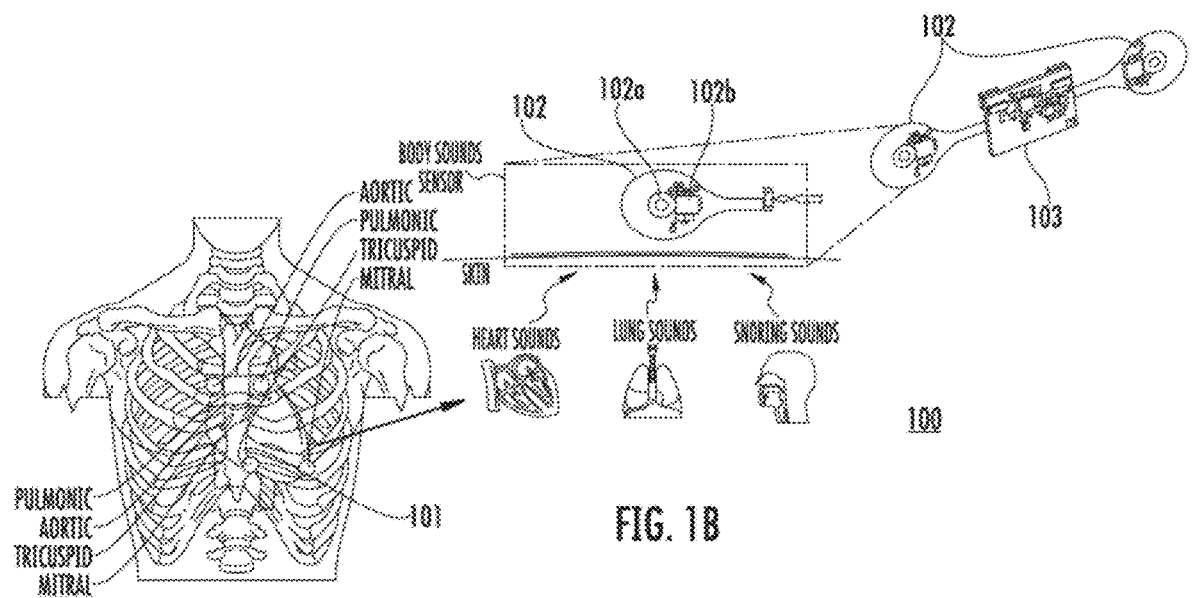
FIGS. 1B and 1C illustrate cardio pulmonary signal capture at the chest in accordance with various embodiments.
Figure 1C:
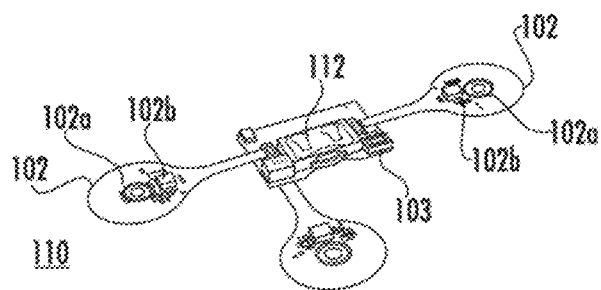

The exemplary embodiments of the system and method proposed here are shown in FIGS. 1A, 1B, and 1C. System 100 shown in FIGS. 1A and 1B is an embedded platform which can be any smart processing platform with digital signal processing capabilities, application processor, data storage, display, input modality like touch-screen or keypad, microphones, speaker, Bluetooth, and connection to the internet via WAN, Wi-Fi, Ethernet or USB. This embodies custom embedded hardware, smartphone, iPad-like and iPod-like devices. Area 101 in FIGS. 1A and 1B is the auditory scene at the chest locations. Array 102 in FIGS. 1A and 1B is the transducer array used to capture the heart signal(s). In some embodiments, the transducer array includes a pad that includes a vibration sensor such as a vibration sensor 102b and an electrode 102a for an ECG sensor. In some embodiments, the transducer array can include a single pad, two pads as shown in FIG. 1B or more than two pads as shown in FIG. 1C. In the particular embodiment of FIG. 1C, a transducer array 110 includes three pads (102) where each pad includes the vibration sensor 102b and the ECG electronic 102a. Other embodiments can include three or more pads where each pad would have at least a vibration sensor and optionally an electrode for the ECG sensor. Hardware 103 in FIGS. 1A-C is the wearable microprocessor hardware with digital signal processing capabilities, application processor, Analog to digital frontend, data storage, input modality like buttons, and wireless connection via Bluetooth, Bluetooth low energy, near field communication transceiver, Wi-Fi, Ethernet or USB.

Processor 112 shown in FIG. 1C comprises of the signal processing module on the wearable device that captures synchronized sensor data from the transducer array 102. The processor 112 is configured to save the synchronized sensor data to memory and communicate it with the system 100 for data transfer. Module 105 in FIG. 1A is the module that calculates vital sign from the input sensor stream coming from hardware 103 for the Heart rate, breathing rate, EKG signal, skin temperature, and associated vitals. The hardware 103 can optionally encrypt the raw sensor data for transmission to the cloud computing module 106. It can also communicate with a dashboard on module 105 or 106 for data exchange, login, alerts, notifications, display of processed data. Computing device 106 in FIG. 1A is the cloud module that processes the individual streams for eventual source separation. In some embodiments, the system 100 could include a connected display or other modality of display or presentation device. In some embodiments the system 100 allows a user to visually see the individual streams and information of the different cardiopulmonary signals.

The transducer array 102 can include multiple sensor transducers that capture the composite signal that includes the electrocardiogram signals, heart sounds, lung sounds and snoring sounds for example. The module 103 can be in the form of wearable hardware that synchronously collects the signals across the transducers and is responsible for the analog to digital conversion, storage and transmission to a portable unit 104. Note that the embodiments herein are not limited to processing the individual streams for source separation, identification and marking of the heart valve signals at the cloud computing module 106 only. Given sufficient processing power, the aforementioned processing can occur at the microprocessor hardware module 103, at the module 105, or at the cloud-computing module 106, or such processing can be distributed among such modules 103, 105, or 106.

Figure 2:
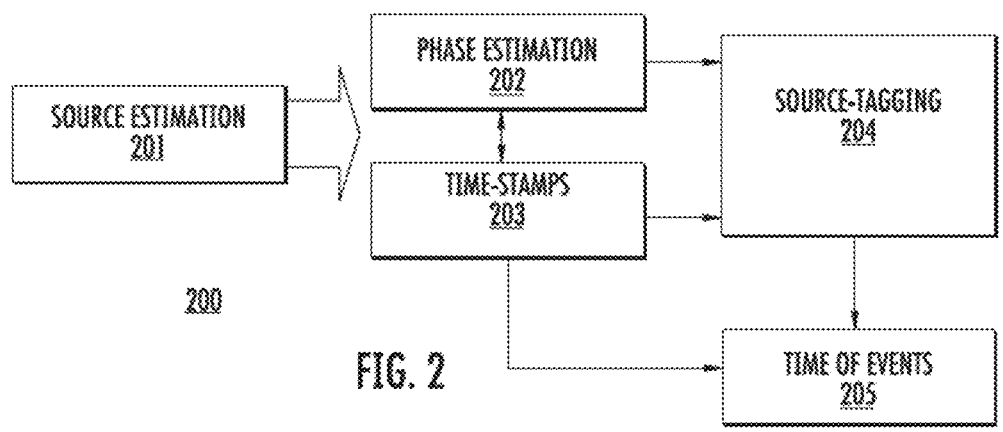
FIG. 2 is a flowchart of a method practiced by the system in accordance with one embodiment.

The exemplary embodiments of the system and method proposed here for the source identification of the cardiopulmonary signals 200 are shown in FIG. 2. Block 201 indicates the separation of sources from the composite signals. Block 202 represents the phase estimation between the separated sources at each of the sensor position. Block 203 represents calculating the time stamps of individual sources at each heartbeat with respect to the synchronized EKG signal and the other sensor or sensors. Block 204 represents the source identification module responsible for tagging each of the separated source in individual heart beats to be one of the heart valve event, namely Mitral valve closing and opening, Tricuspid valve closing and opening, Aortic valve opening and closing, and the Pulmonic valve opening and closing. Block 205 represents the time marking module to estimate the time of occurrence of the above mentioned valve events with respect to the start of the EKG signal.

Figure 3:
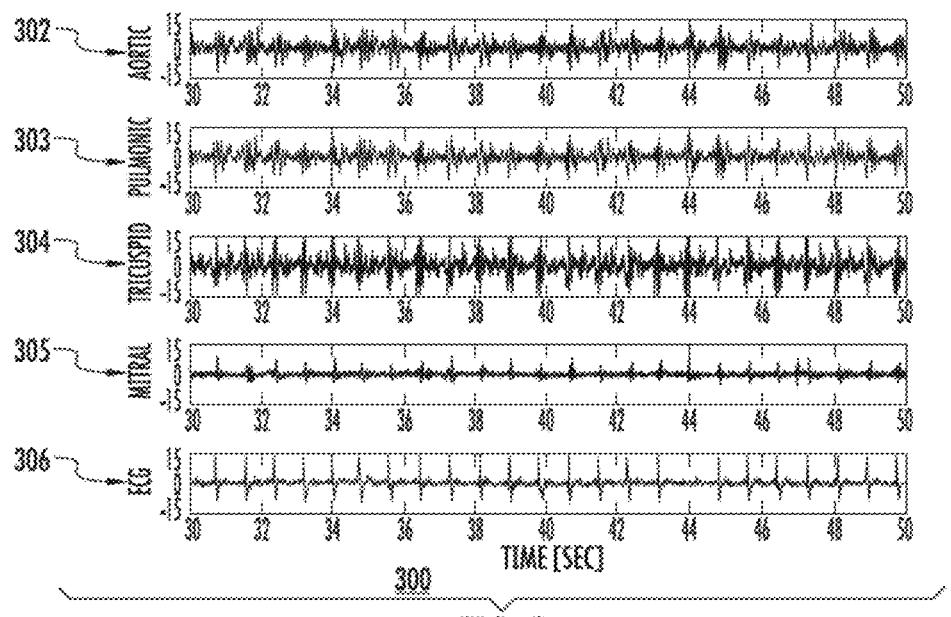
FIG. 3 illustrates multichannel signals captured from the sensor array on the chest shown in accordance with one embodiment.

The exemplary embodiments of the system and method proposed here for the source identification of the cardiopulmonary signals from the composite signal 300 are shown in FIG. 3. Area(s) 101 in FIG. 1B indicate the locations at which the composite heart signal can be captured. A vibration signal 302 as charted on the first line in FIG. 3 represents a signal captured at the aortic auscultation location. A vibration signal 303 shows the vibration signal captured at the pulmonic auscultation location. A vibration signal 304 shows the vibration signal captured at the tricuspid auscultation location. A vibration signal 305 represents a vibration signal captured at the mitral auscultation location. The last or bottom line in FIG. 3 represents an electrocardiogram signal 306 captured. In some embodiments, note that the number of sensors used (such as in the sensor array 102 of FIG. 1), are less than the number of vibration sources. For example, 3 sensors can be used to ultimately extract signals for 4 (or more) vibration sources; or 2 sensors can be used to ultimately extract signals for 3 or 4 (or more) vibration sources; or 1 sensor can be used to ultimately extract signals for 2, or 3, or 4 (or more) vibration sources.

Figure 4:
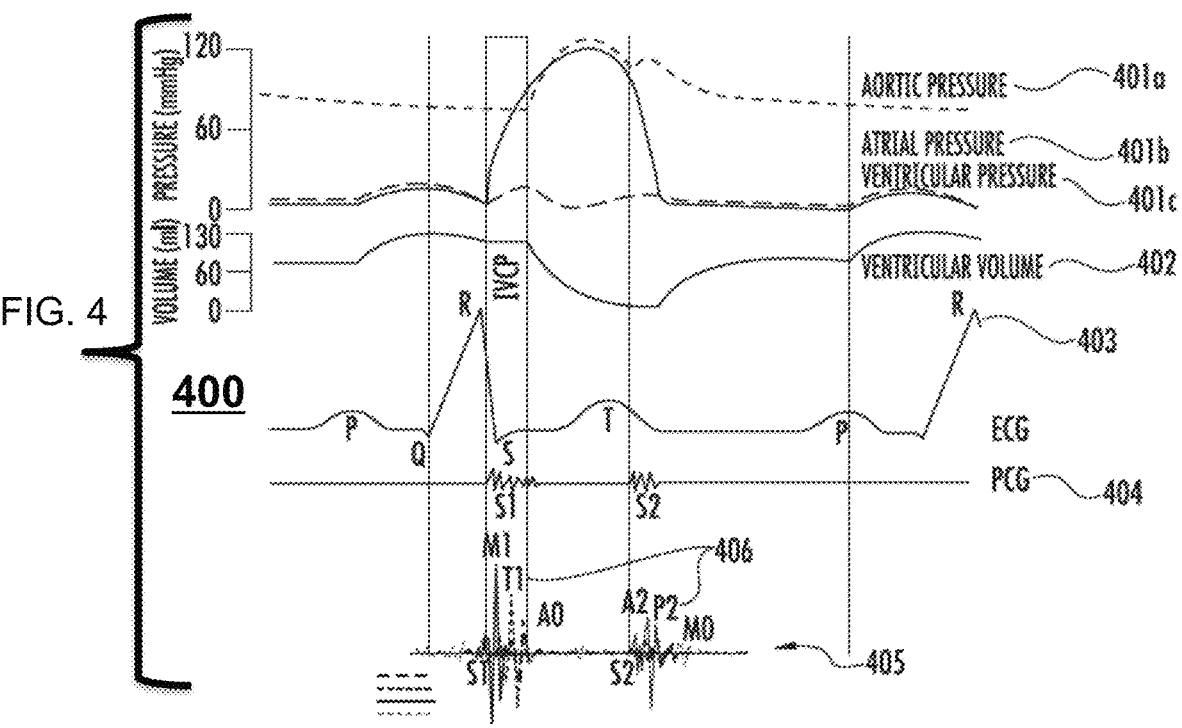
FIG. 4 illustrates a cardiac cycle in relation with Electrocardiogram, acoustic and accelerometer sensors of the system in accordance with one embodiment.

The exemplary embodiments of the system and method proposed here draw inspirations from biology with respect to the cardiac cycle in-relation with electrocardiogram and accelerometer transducer captured cardiac signal. A timeline chart 400 in FIG. 4 shows a cardiac cycle. Lines or signals 401a, 401b, and 401c represent or indicate the pressure changes during a cardiac cycle for aortic pressure (401a), atrial pressure (401b) and ventricular pressure (401c) measured in measured in millimeters of mercury (mmHg). Line or signal 402 represents or indicates the volume changes during a cardiac cycle in milliliters (ml). Line or signal 403 represents or indicates the electrical changes during a cardiac cycle captured by an electrocardiogram. Line or signal 404 represents or indicates the acoustic changes during a cardiac cycle captured by an acoustic sensor such as a phonocardiogram or PCG. S1 represents the first heart sound or the "lub" sound and the S2 represents the second heart sound or "dub" sound. Line or signal 405 represents or indicates the vibration changes during a cardiac cycle captured by an accelerometer transducer at the location of the device. Pattern 406 in FIG. 4 indicates the different valve opening and closing seen in line or signal 405 as captured by the accelerometer sensor or sensors. More specifically, a closer inspection of the pattern 406 reveals the closing of the mitral valve (M1) and tricuspid valve (T1) during the S1 or first heart sound and the closing of the aortic valve (A2) and pulmonary valve (P2).

Figure 5:
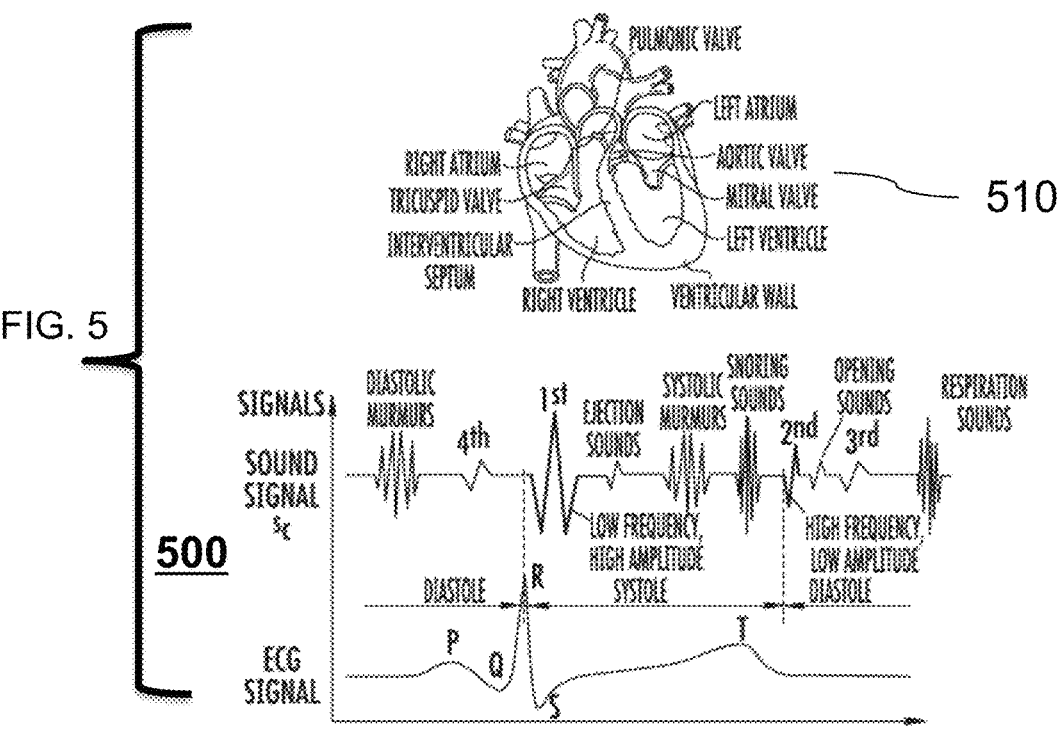
FIG. 5 illustrates a heart anatomy and schematic representation of the cardiopulmonary sounds in relation to electrocardiogram.

FIG. 5 goes on to further show a representation 510 of the human heart relevant for the generation of the sounds and corresponding graph 500 representing the sounds belonging to coronary artery, murmurs, first sound, second sound, third sound, fourth sound, ejection sounds, opening sounds, respiratory sound, breathing, and snoring during individual heart beats, with respect to the electrocardiogram signal.

The exemplary embodiments of the system and method proposed here provide a source marking algorithm for the vibrations from the cardiohemic system. In some embodiments, the system next uses PCA to determine which source is associated with which event (e.g., Mitral closing & opening, Tricuspid closing & opening, Aortic opening & closing, Pulmonic opening and closing). The following describes the architecture for automatic source tagging and timing of valvular events. One way to identify which events are relevant to a source is by manually tagging the sources against the synchronized EKG signal and taking advantage of the timings relative to a QRS wave (identification of the S1 and S2 sounds using the EKG signal as the reference has been widely researched in studies). Another approach is an automatic tagging algorithm. The tagging is composed of a classifier preceded by a feature extraction algorithm. For the timing, the system exploits the computations of one of the feature extraction algorithms to obtain an energy contour from which the time location of a given event can be inferred. Because the embodiments here build upon having the ability to capture the signal at different locations simultaneously, to the proposed system exploits the relations among channels to extract additional information about the sources. Likewise, since some source separation algorithms where channels relations are associated with location, the system can leverage on the intrinsic relations among the channels to extract relevant information that helps the system distinguish among the events. In some embodiments, the system hypothesizes that phase information between channels is relevant for distinguishing among cardiac events since valves are located at different positions within the heart. Perhaps, one of the most distinctive features of the cardiac events is their relative order of occurrence, which repeats periodically with each heartbeat. Time information extracted from the set of sources can be utilized to localize the occurrence of each source signal within the heart cycle. Therefore, the features proposed here are conceived to provide three aspects: 1) Spectral information, 2) Relations among channels, and 3) Relations among events in the form of relative times of occurrence.

The automated timing is obtained from the separated sources. The embodiments can employ the eigenfilter approach described above to extract energy envelopes that can be easily detected and further processed to extract a time point. In this case, the system uses the two leading right singular vectors of the tap-delay matrix. It has been observed that, for a single channel, the first two right singular vectors of the tap-delay matrix contain oscillatory components with $\pi/2$ phase delay. This behavior can be extended to the two-channel case by noticing that the first half of the two leading singular vectors contain an oscillatory component of similar frequency with the above mentioned $\pi/2$ phase difference for channel 1, and that the same result applies to the second half for channel 2. From the above observation, we can consider the first 2 leading right singular vectors as a quadrature pair of eigenfilters. In other words, these filters have the same magnitude in frequency with a $\pi/2$ phase difference. The sum of instantaneous energies for the quadrature pair provides an energy envelope that, for the source signals, can be processed in a simple way to obtain time stamps on the occurrence of the events associated with the source. Let u1 and u2 be the two leading right singular vectors of $\Delta i$. Let $s_1 = \Delta_i u_1$ and $s_2 = \Delta i u_2$ be the score vectors. The energy envelope s can be calculated as $(s)_i = (s_1)_i^2 + (s_2)_i^2$. From the sparsity property of the heart sounds, it is possible to detect single heart beats from the energy contour s since the source signal is mostly zeroes followed by the oscillations related to the event at each heart beat. A simple marking procedure can be obtained by first detecting individual heartbeats and then processing the cumulative energy within a heartbeat to set a threshold that defines the marking point. Process 602 shown in the box 610 of FIG. 6B describes the procedure. A resulting time stamp (black vertical lines) 601 (in chart 600 of FIG. 6A) using the energy threshold can be marked. Notice that the endpoints of the Heart valve signal have been also detected as part of the procedure in determining the time stamps 601. The chart 600 shows the resulting markings using a cumulative energy to provide a threshold. In this case 1% of cumulative energy was selected to provide the threshold value. Chart 603 shows the time intervals found for the Mitral closing (611), Tricuspid closing (612), Aortic opening (613), Aortic closing (614) and Pulmonic closing (615).

The exemplary embodiments of the system and method proposed here provide a source marking algorithm that allows from the explanation earlier for the marking of the Mitral valve closing (MC), Mitral valve opening (MO), Aortic valve opening (AO), Aortic valve closing (AC), Tricuspid valve closing (TC), Tricuspid valve opening (TO), Pulmonary valve closing (PC) and Pulmonary valve opening (PO) signals. The extracted individual valve vibration objects are aligned into a signal for each of the four valves across multiple heart beats. The chart 700 in FIG. 7A shows the source separation of heart valve opening and closing signals. Line 701 indicates the length or duration of the vibration signal for the Mitral valve closing (M1). Line 702 indicates the length or duration of the vibration signal for the Tricuspid valve closing (T1). Line 703 indicates the length or duration of the vibration signal for the Aortic valve closing (A2). Line 704 indicates length or duration of the vibration signal for the Pulmonic valve closing (P2). Signal 705 indicates the composite vibration signal captured by a particular transducer. Signal 706 indicates the EKG signal captured by the system. Referring to chart 710 of FIG. 7B, the Line 707 indicates the length or duration of the vibration of the Aortic valve opening (AO). Line 708 indicates the length or duration of the vibration of the Pulmonic valve opening (PO). Further note that the lines or signals 709 in FIG. 7A or 711 in FIG. 7B are actually several separated superimposed signals representing the vibration signals from separate sources coming from the mitral valve, tricuspid valve, aortic valve, and pulmonary valve (using less than 4 vibration sensors to extract such separated signals in some embodiments.

Figure 8A:
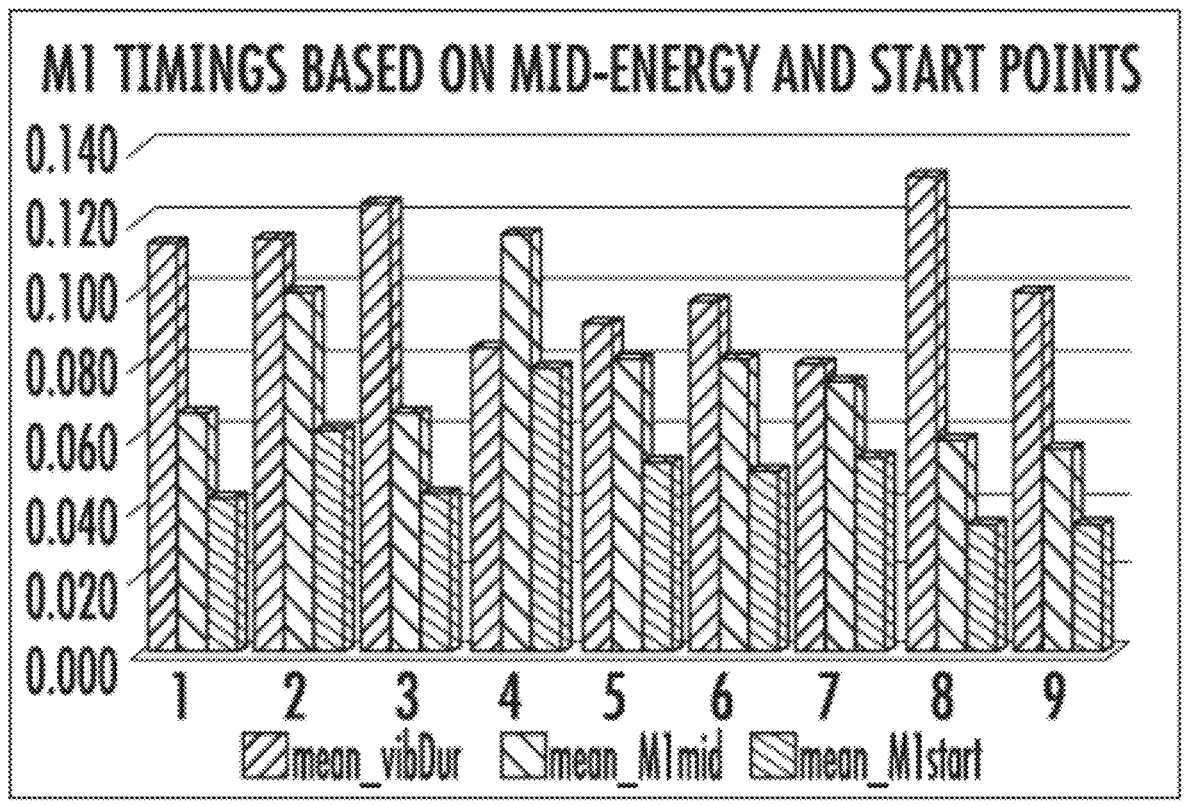
FIGS. 8A, 8B, and 8C illustrate the comparison of M1, T1, A2, and P2 timings and comparison of time calculations using different energy thresholds in accordance with one embodiment.
Figure 8B:
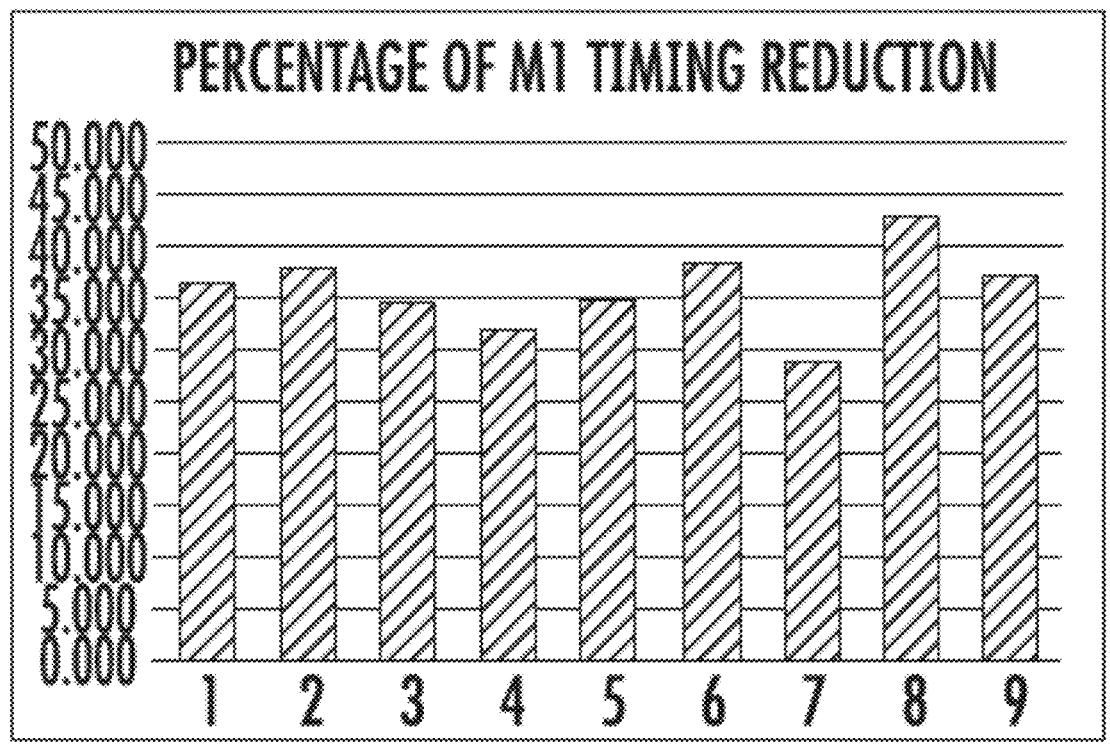
Figure 8C:
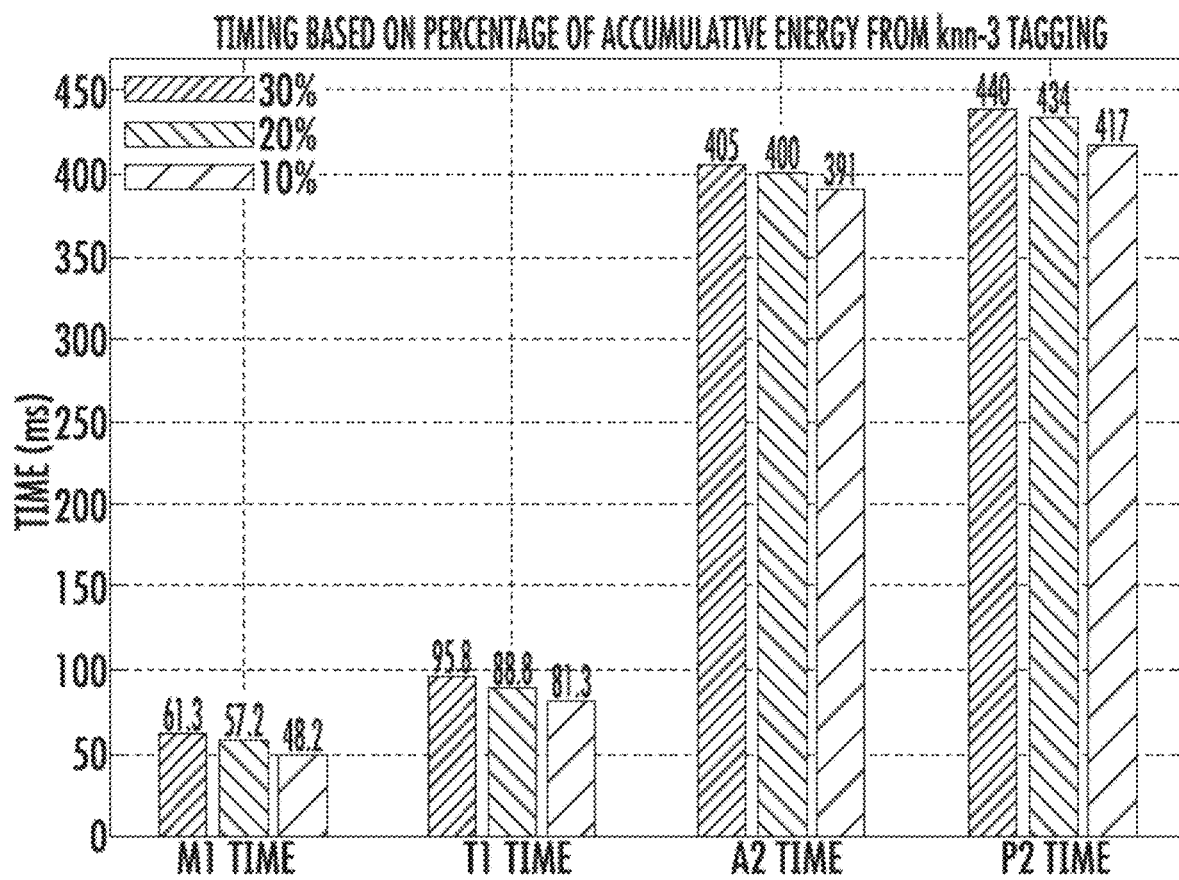

It was observed that peak of T1 timing distribution is close to that of AO. The reason is that the length of M1 and T1 Source Separation vibrations is longer than the length of AO Source Separation vibrations. So when the mid-point of accumulative energy is calculated, M1 and T1 timings are already shifted forward and don't represent the start of the vibration. Such a timing shift exists for AO but it's not as big as M1 and T1. To verify and compare, the following time information on some patients helps provide different approaches: Mean length of M1, T1 vibration, Mean start point of M1, T1 vibration, Mid-energy point is obtained from PCA algorithm. A shift back in timing of M1, T1, A2, P2 by reducing the 50% of accumulative energy to 30%, 20%, and 10%. The results are demonstrated in FIGS. 8A, 8B and 8C.

In the exemplary embodiments, a novel way of calculating the timing of the source separated individual heart vibration events from the composite vibration objects captured via multiple transducers is used to work on a single package, easy-to-use and portable device.

The exemplary embodiments develop a novel method of source timing, which in one embodiment using the Pulmonary and Aortic, and in addition possibly the Tricuspid and Mitral auscultation locations, lends the system capable of calculating the time intervals of individual valve events from the vibrations with respect to the electrocardiogram.

The exemplary embodiments develop a novel method of time interval calculation, which in one embodiment using the Pulmonary and Aortic, and in addition possibly the Tricuspid and Mitral auscultation locations, lends the system capable of marking the time of occurrence of the individual valve events with respect to the electrocardiogram. The novel method lends the system capable of measuring the cardiac time intervals.

The exemplary embodiments develop a novel method of providing time intervals of individual valve signals over time. The novel method allows for both short-term and long-term discrimination between signals. Short-term pertains to tracking individual stream when they are captured simultaneously as part of the composite signal. Long-term tracking pertains to tracking individual streams across multiple heart beats, tracking valve signals as they transition in and out during each cardiac cycle.

The exemplary embodiment of system and method described is the development on an embedded hardware system, the main elements required to capture body sounds are the sensor unit that captures the body sounds, digitization, and digital processing of the body sounds for noise reduction, filtering and amplification. Of course, more complicated embodiments using the techniques described herein can use visual sensors, endoscopy cameras, ultrasound sensors, MRI, CT, PET, EEG and other scanning methods alone or in combination such that the monitoring techniques enable improvement in terms of source separation or identification, and/or marking of events such as heart valve openings, brain spikes, contractions, or even peristaltic movements or vibrations. Although the focus of the embodiments herein are for non-invasive applications, the techniques are not limited to such non-invasive monitoring. The techniques ultimately enable diagnosticians to better identify or associate or correlate detected vibrations or signaling with specific biological events (such as heart valve openings and closings, brain spikes, fetal signals, or pre-natal contractions.)

The exemplary embodiments herein provide a method and system based on a technique to identify the separated cardiopulmonary signals, to extract information contained in vibration objects. In one embodiment, known under machine learning, auditory scene analysis, or spare coding approaches to the source separation problem. Data is obtained using a tri-axial accelerometer or multiple tri-axial accelerometers placed on different points of torso.

Examples of cardiac vibration objects are the first sound, the second sound, the third sound, the fourth sound, ejection sounds, opening sounds, murmurs, heart wall motions, coronary artery sounds, and valve sounds of the Mitral valve opening and closing, Aortic valve opening and closing, Pulmonary valve opening and closing, Tricuspid valve opening and closing. Examples of the pulmonary vibration objects are the respiratory lung sounds, breathing sounds, tracheobronchial sounds, vesicular sounds, Broncho vesicular sounds, snoring sounds. A portion of the energy produced by these vibrations lies in the infra-sound range, which falls in the inaudible and low sensitivity human hearing range. A portion of the energy produced by these vibrations falls in the audible hearing range. Accelerometer transducers placed on the chest capture these vibrations from both these ranges.

Source identification analysis in accordance with the methods described herein identify individual vibration objects described above from the source separated vibration signals. The individual vibration signals are identified to be from the mitral valve, aortic valve, tricuspid valve, the pulmonary valve, coronary artery, murmurs, third sound, fourth sound, respiratory sound, breathing, and snoring during individual heart beats. The identified signals are marked to indicate their start with respect to the start of the EKG.

The embodiments can include different source identification techniques specifically used for tagging the individual cardiopulmonary signals for application in a non-linear time variant system, such as Principal component analysis, Gabor filtering, Generalized Cross Correlation (GCC), Phase transform (PHAT), ROTH, SCOT and Band Filtering. Using 1) Spectral information, 2) Relations among channels, and 3) Relations among events in the form of relative times of occurrence.

The exemplary embodiments provide a novel approach for small, portable, robust, fast and configurable source separation based software with transducer hardware 103, 203. The use of the vibration signal pattern and novel psychoacoustics help bypass conventional issues faced by linear time invariant systems.

The following are the various types of heart disease that can be diagnosed and treated using the identifies signals, namely, Coronary artery disease, Heart murmurs and valve abnormalities, Heart failure, Heart rhythm abnormalities (arrhythmias), Vascular disease, congenital heart disease, and Risk factor modification. A physician can work with patients to perform a comprehensive evaluation and design a personalized plan of care aimed at keeping them healthy.

In another embodiment, the source can be identified by manually tagging them against the synchronized EKG signal and taking advantage of the timings relative to the QRS wave. This way, however is usually slow and time consuming and an automatic tagging algorithm is thus preferable. Since the different heart sounds comes from different locations in the heart, it is expected that each source will have a unique phase relation between the sensors that are located at fixed points during the data gathering phase. This phase relation can be made evident by using signal representation with a dictionary suited for highlighting frequency and phase relations with a greedy algorithm such as the matching pursuit. Our algorithm performs a Gabor analysis in the source separated signals using a finite Gabor Dictionary of fixed frequencies and with variable phase delay. The system finds the delay that minimizes the reconstruction error for each source and creates a group of features that will be incorporated into a decision-making and classification algorithm. The classification algorithm will combine the features extracted by the Gabor analysis with other features that comes from the PCA and cross correlation analysis that uses a set of manually tagged patient's tracks as training. The system is composed of three modules or stages: A suitable Gabor dictionary is created that can serve as the basis representation of the signals. An optimization algorithm aims to find the delay that will minimize the reconstruction error in a giving delay range. Collection and organization of all the features extracted from the second stage. For each one of the stages different techniques were tried in order to achieve the best results. The Gabor dictionary selected has the function:

$$G(\theta, n) = e^{-\frac{1}{2}\frac{(n-\theta)^2}{\sigma^2}} \cos\left(4\pi \frac{n-\theta}{f}\right)$$

In the equation $\theta$ is the delay, $\sigma$ is the Gaussian decay of the atom and f is the frequency of operation of the Gabor. The system initially searched for the Gabor atoms that best represented the signal by doing a sweep in frequency and selecting those Gabor atoms that produced a larger weight matrix after the matching pursuit. The system was subsequently changed to a group of fixed frequency Gabor atoms exploiting the fact that for the M1, T1, A2 and P2 sounds vibration reside mainly in the range of 50-300 Hz and the Aortic opening vibration resides mainly in the low frequency range (from 0-50 Hz). The fixed Gabor approach sacrifices a little bit of reconstruction error in favor of a faster computation and easier analysis since the frequencies were fixed. The first optimization technique used was the, Gradient Descent algorithm: A first-order optimization algorithm that looks for the minimum of a given function by taking steps proportional to the negative of the gradient. The system is very dependent on the initial guess and number of minima of the system. A second approach was using the minimize function, which uses the Polack-Ribiere algorithm of conjugate gradients to compute search directions, and a line search using quadratic and cubic polynomial approximations. The system is also dependent on the initial value of the search but is more efficient in choosing the parameters to find the minimum. Finally, a brute force approach was implemented that sweeps the signal with different delays and then selects the one that resulted in a minimum function. In order to improve speed on this algorithm, a broad search is done first and then a refined search is done around the minimum point found by the broad search.

The exemplary embodiments of the system and method proposed here provide a source identification algorithm for the vibrations from the cardiopulmonary system. In order to find the time stamps for events such as Mitral closing & opening, Tricuspid closing & opening, Aortic opening & closing, Pulmonic opening and closing, we look at all the individual source separated signals 701 to 706 of the composite signal 707 and first tried to find the location of max peak in the SS signal for each source and then find delay between two channels. 708 shows the frequency spectrum of the source separated signals. Cross correlated vibrations in aortic and pulmonic channels for each interval for each source are calculated to find a consistent delay between two channels 709. Given the start of QRS and end point of each vibration, the vibration(s) within this interval is cross correlated with all vibrations in each source. This is done for both aortic and pulmonic channels. At the end, Principle Component Analysis (PCA) was applied to find the timing information and delay between two channels. PCA uses SS signal from each source in each channel to find the template which represents majority of the vibrations within that source. The template is then cross correlated with the whole source and max of PCA signal in each interval is found and compared with the start of QRS. In another implementation, In the second attempt, SS signals from two channels but the same source are fed into PCA to find the template. Then aortic template is used for both channels' cross correlation to identify the different vibrations into valve events, breathing sounds, and vibrations of the heart walls. To accurately estimate M1, T1, A2, P2, A0, P0 from the frequency signal captured by digital accelerometer on the wearable, several sub-frequencies are considered. Some are noted here for example: 0-30 Hz, 0-60 Hz, 30-150 hz, 30-250 Hz.

The exemplary embodiments of the system and method proposed here provide a source marking algorithm for the vibrations from the cardiopulmonary system. Next step is to use PCA to determine which source is associated with which event (Mitral closing & opening, Tricuspid closing & opening, Aortic opening & closing, ulmonic opening and closing). We describe the architecture for automatic source tagging and timing of valvular events. One way to identify which events are relevant to a source is by manually tagging the sources against the synchronized EKG signal and taking advantage of the timings relative to the QRS wave (identification of the S1 and S2 sounds using the EKG signal as the reference hast been widely researched in studies. Another approach is an automatic tagging algorithm. The tagging is composed of a classifier preceded by a feature extraction algorithm. For the timing, we exploit the computations of one of the feature extraction algorithms to obtain an energy contour from which the time location of a given event can be inferred. Because our work builds upon having the ability to capture the signal at different locations simultaneously, we want to exploit the relations among channels to extract additional information about the sources. Likewise some source separation algorithms where channels relations are associated with location, we leverage on the intrinsic relations among the channels to extract relevant information that helps us distinguish among the events. We hypothesize that phase information between channels is relevant for distinguishing among cardiac events since valves are located at different position within the heart. Perhaps, one of the most distinctive features of the cardiac events is their relative order of occurrence, which repeats periodically with each heartbeat. Time information extracted from the set of sources can be utilized to localize the occurrence of each source signal within the heart cycle. Therefore, the features we propose here are conceived to provide three aspects: 1) Spectral information, 2) Relations among channels, and 3) Relations among events in the form of relative times of occurrence. We describe a feature extraction algorithm based on multichannel Gabor basis decomposition using matching pursuit, and a second algorithm that uses eigendecomposition of a covariance matrix extracted from the source signals to obtain a cross correlation function between channels. For the gabor basis, consider the reconstruction of a 2-channel signal x (t). In this approach we want to extract a phase relation between the sensors which are located at standard aortic and pulmonic auscultation positions. As we mentioned above, we are interested on features that reflect spectral content as well as the channel interrelations. In the two channel case, each basis function is a pair of Gabor functions with equal frequency f and envelope width h and a phase difference θ. The tunable parameter θ can be swept across a range of values for which the matching pursuit reconstruction error can be obtained. The behavior of the reconstruction error for a source signal over different values of θ provides information about the phase different between the two channels for the particular source signal. In particular, the value of θ that attains the minimum error within the defined range of values is taken as the optimal channel delay, and the time average of the activation coefficients obtained by matching pursuit at the optimal θ provide and spectral characterization of the source. For the feature Extraction by Self-Similarity Template Based-on PCA, we define a self-similarity using the concept of eigenfilter. Let yi the a two-channel source signal defined in (1), and let Yi its discretized version of size N×2. For filter of length Nw, we compute the tap-delay matrices $\Delta(j)$. The joint-channel eigenfilter correspond to the leading right-singular vector u of the tap-delay centered matrix $\Delta i$ obtained by removing the mean of each column of $\Delta i$. The eigenfilter u can be split into the first and second channel components. The first channel component u(1) corresponds to the first Nw entries of u, and u(2) to the remaining entries going from index Nw+1 to last index 2Nw. The proposed feature is the cross-correlation function between u(1) and u(2). Note that this function contains the main frequency components of the source signals expressed in the time domain and the peak provides information about the channel relations. For different delays between the two channels the cross correlation peaks at different locations, accordingly. To extract relative time information contains cues for the classification of the cardiac events, we adopt a simple approach that uses the energy contours. The process consists of three basic steps: Compute energy contours for all source signals, Compute timings for each source signal, Compute features of source i by averaging the sum of the remainder sources centred at the timings. The energy of each source signal Yi is calculated using the leading, quadrature pair of right singular vectors of their corresponding tap-delay matrix. For classification, a set of training exemplars (sources) have been manually tagged with the respective events. Each source signal is then represented by the feature vectors described above. Test have been carried out on pooled covariance linear discriminant analysis, quadratic discriminant analysis, k-nearest neighbours and support vector machines both linear kernel and Gaussian kernel. The features described in the previous sections can be used in different manners for tagging, for example: Tagging using only Gabor-based features, Tagging using only self-similarity features, Tagging using only time-based features, Tagging using all Gabor-based, self-similarity, and time-based features. There are even sub cases of the situations considered above, For instance, the combination of Gabor and self-similarity features can be done on a single classifier or using ensembles. The first validation examples only address the cases in the bullet items. In addition to the classifier, preprocessing of the feature vectors is also performed. A centering vector $x_{cent}$ is calculated using the mean over the training set $X_{train}$. This step is followed by a linear transformation based on PCA to produce a much smaller dimension feature vector. The preprocessing is summarized in Algorithm 1, FIG. 9. The choice of p is typically driven by the training data itself. The singular values of $X_{train}$ can be used to decide the dimensionality of the transformed feature vectors after.

The exemplary embodiments of the system and method proposed here provide a source marking algorithm that allows from the explanation earlier for the marking of the Mitral valve closing (MC), Mitral valve opening (MO), Aortic valve opening (AO), Aortic valve closing (AC), Tricuspid valve closing (TC), Tricuspid valve opening (TO), Pulmonary valve closing (PC) and Pulmonary valve opening (PO) signals. The extracted individual valve vibration objects are aligned into a signal for each of the four valves across multiple heart beats. 800 in FIG. 8 show the source separation of heart valve opening and closing signals. 801 indicate the vibration signal for the Mitral valve closing. 802 indicate the vibration signal for the Tricuspid valve closing. 803 indicate the vibration signal for the Aortic valve closing. 804 indicate the vibration signal for the Pulmonic valve closing. 805 indicate the composite vibration signal captured by a particular transducer. 806 indicate the EKG signal captured by the system. 807 indicate the vibration of the Aortic valve opening. 808 indicate the vibration of the Pulmonic valve opening.

The exemplary embodiments of the system and method proposed here provide a source marking algorithm for the vibrations from the cardiopulmonary system, using information about the time of occurrence of the event. Automated finding of M1, T1, A2 & P2: After going through the timing plots of different patients, it was decided to first determine A2 and P2 timing and their corresponding sources and then find M1 and T1 from the rest of sources. Automatic A2 & P2 finding: 1) The number of zero-crossings is found for each SS source. Then the noisy source that is associated with the maximum zero-crossing is discarded. 2) Automated calculation of QRS onset points for all heartbeats in each source. 3) Automated calculation of beginning and ending points of all vibrations in each source. 4) Applying PCA approach on all sources that outputs the time difference between QRS onset and peak of PCA signal (timing vector) as well as delay between aortic and pulmonic channels. 5) Based on probability density estimation of each source's timing vector, strong peak(s) that correspond(s) to timing(s) more than 300 ms are accepted as A2 and P2 candidates and those sources that don't satisfy this condition are discarded. Also new candidate timings are sorted in ascending order. 6) Variation, length of samples more than 300 ms (L) and some other measurements are calculated from accepted timing vectors of accepted sources and are stored in a structure for further analysis. 7) If there is only one strong peak in probability density estimation plot whose timing is more than 300 ms, then a variable called "ind_both" is set to 1. If there are two or more strong peaks whose timing is more than 300 ms, if max peak's timing is over 300 ms, then "ind_both" variable is set to 1 but if max peak's timing is lower than 300 ms but another strong peak's timing is more than 300 ms, then "ind_both" is set to 0. If there are two or more sources whose "both_indic" variables are equal to 1, then "both_indic"=1.8) In case of having no valid timing, A2 and P2 are set to zero. 9) In case of having one valid timing, if L>6 then it is marked as A2 and its corresponding source number is also saved. P2 is set to zero. 10) In case of having two valid timings:

```
if both_indic =1 ,
    if L1 >=6 samples, then A2 is set to first timing in sorted timing vector Else A2=0
    if A2=0 and L2 >=6, then A2 is set to second timing in sorted timing vector Else P2=0
    if A2 ~=0 and L2 >=6, then P2 is set to second timing in sorted timing vector Else P2=0
if both_indic ~=1 ,
    if L1 >= 4 samples & V1<=800 then A2 is set to first timing in sorted timing vector Else A2=0
    if A2=0 and L2 >=4 & V1<=800 , then A2 is set to second timing in sorted timing vector Else P2=0
    if A2 ~=0 and L2 >=6 & V2<=800 then P2 is set to second timing in sorted timing vector Else P2=0
11)In case of having more than two valid timings,
if both_indic =1
for loop: if L1 >=6 & V1<=800, then A2 is set to current timing in sorted timing vector;
break     Else A2=0; End of for loop
    if A2=0, then P2 = 0;
    if A2~=0 & last timing in the sorted timing vector
        if L >=6 & V1<=800, then P2 is set to last timing in the sorted timing vector
    if A1~=0 & there are two timings after A1 timing,
        if V2<V1, then P2 is set to second timing after A2.
        Else P2 is set to first timing after A2.
    if A1~=0 & there are more than two timings after A1 timing,
        if L1 >=6 & V1<=800 , then P2 is set.
if both_indic ~=1 ,
for loop: if L1 >= 8 samples & V1<=1000 then A2 is set to current timing in sorted
timing vector Else A2=0; End of for loop.
    if A2=0, then P2 = 0;
    if A2~=0
for loop: if L >=8 & V1<=1000,
            then P2 is set to current timing in the sorted timing vector; break
            Else P = 0;
End of for loop
```

At the end A2 and P2 timings and their corresponding source numbers are saved in an excel with a long with patient name. Automatic M1 & T1 Finding:

```
1) The same previous steps from 1 to 7 are implemented in this phase
8) In case of having no valid timing, M1 and T1 are set to zero.
9) In case of having one valid timing, if L > 6 and timing is less than 120 ms,
    then it is marked as M1 and its corresponding source number is also saved.
    P2 is set to zero.
10)In case of having two valid timings,
if both_indic =1 ,
    if L1 >=6, then M1 is set to first timing in the sorted timing vector Else M1 =0
    if M1 =0 & L2 >=6, then M1 is set to second timing in the sorted timing vector and T1=0
    if M1~=0 & L2>=6 and second timing is less than double the first timing
        then T1 = second timing in the sorted timing vector Else T1 =0
if both_indic ~=1
L1>=4 & V1<=800, then M1 is set to first timing in the sorted timing vector Else M1 =0
If M1=0 & L2>=4 & V2<=800, then M1 = second timing in the sorted timing vector Else
```

```
T1 = 0
If M1~=0 & L2>=4 & V2<=800, then T1 = second timing in the sorted timing vector Else
T1 = 0
    11) In case of having more than two valid timings,
if both_indic ~=1 ,
for loop: if L >=8 & V<=1000, then M1 is set to current timing in the sorted timing vector
        Else M1 =0; break; end of for loop
    if M1 =0, then T1 = 0;
for loop: if M1~=0 & L >=6 & V<=1000, then T1 is set to current timing in the sorted
timing vector; break, end of for loop
if M1~=0 & L2>=6 and second timing is less than double the first timing
        then T1 = second timing in the sorted timing vector Else T1 =0
if both_indic =1
low_ var = Find sources with variations less than 15.
From these low_var sources, find those whose length are more than 9
samples(len_low_var).
If length of low_var >=2 & len_low_var >=2
        M1 is set to the timing corresponding to the lowest variation
        T1 is set to the timing corresponding to the second lowest variation
Else
for loop: If L >=5 & V<800, then M1 is set to the current timing in the sorted timing
vector Else M1=0
If M1 =0, then T1 =0
If M1~=0
for loop:
If there is only one timing after M1 & L >=5 & V <=800, then T1 = current timing in the
sorted timing vector; break
If there are two timings after M1,
if V1 < 300, then T1 = first timing after M1 in the sorted timing vector; break
Elseif V2<V1, then T1 = second timing after M1 in the sorted timing vector; break
Else, T1 = first timing after M1 in the sorted timing vector; break
If there are more than two timings after M1,
if V1 < 5, then T1 = current timing after M1 in the sorted timing vector; break
Elseif V2<V1, then T1 = current timing after M1 in the sorted timing vector; break
Else, T1 = current timing after M1 in the sorted timing vector; break
---
```

Automated Finding of Aortic Opening (AO):
  Track 1 with 2 channels 8 by 2 by N
  M1, T1 timings and EKG times
  Remove the noisy source using max zero-crossing. Data down to 7 by 2 by N
  Sub-source markings including start and end of vibrations, envelope and max peak
  Save to non-zero-source vector for both channels
  Remove missing start and end points and too large ones by comparing between two channels as well as considering each source
  Calculate PCA for two channels and all vibrations. Outputs are delay_vec, PCA signal and delay between two channels
Begin AO Detection
  Select above data for AO channel
  Remove zero delay values
  Remove delays between two channels that are greater than 50 ms and count<4
  Remove positive delays between two channels and count<5
  Calculate ksdensity
  Find max peak as well as other peaks that their distance together is more than 5 samples
  Keep negative delays if delay is less than 150 ms
  Calculate ksdensity of event_vec
  Find more max peak and peaks>half of max peak
  Find peaks>10 ms and with 0.05 of max probability value
  Save all the candidate sources with negative delay btw two channels
  Select peaks that fall in range of M1 and M1+95 ms (if M1=T1=0, in range 20 to 150 ms)
  Sort all timings and save
  Find AO
First case: If there is only on candidate source:
  1) If delay variation<500 but source variation>1000,
  2) remove timings>200 ms,
  3) If length of samples>4, remove samples whose timings relative to median are >60 ms
  4) If empty timing vector:
I. then get the original timing vector, calculate kdensity and find max and other peaks whose probability is more than half of max's probability
II. If time diff btw AO candidate and max peak's timing<10 ms,
  set max's peak timing as ref time, remove samples with diff more than 50 ms relative to ref time and update the AO candidate and its variation.
III. If time diff btw AO candidate and max peak's timing>10 ms,
  find a qualified peak and its corresponding timings that is closest to AO candidate, set that peak's timing as ref time, remove samples with diff more than 50 ms relative to ref time and update the AO candidate and its variation.
  5) If non-empty timing vector:
I. calculate kdensity and find max and other peaks whose probability is more than half of max's probability. Find the one that is closest to candidate, set is as ref time, remove samples with diff more than 50 ms relative to ref time and update the AO candidate and its variation.
  6) Check if var_delay<500 && var_SRC<900 && AO_candidate<=M1+96

Second case: If there are two candidate sources:
The following steps from the first case are implemented:
1, 2, 3 with 50 ms threshold, and 6
After founding all valid AO timings from all candidate sources, the closet AO candidate to "M1+30 ms" is selected.
Third case: If there are more than two candidate sources:
The following steps from the first case are implemented:
1, 2, 3 with 90 ms threshold, 4 with 90 ms threshold, and 6
After founding all valid AO timings from all candidate sources, the closet AO candidate to "M1+30 ms" is selected.

To improve the results in the exemplary embodiment we develop AO detection using new PCA approach such as: Mean removal, Min-Max removal, Different window length for correlation. Detailed analysis on delay calculation from cross-correlation template. Source tagging using PCA features and different classifiers on both tagged and untagged tracks for both High Pass and Low Pass. Defined two timing calculation algorithm 1) with threshold 2) without threshold and got the timing distributions for different test cases. To improve AO detection using new PCA algorithm, a few different tests were done such as: Removed the mean of each source's template (X matrix) before calculating covariance matrix. For some sources, cross-correlation template shows zero delay at a discontinued point although there is a delay between peaks of templates. Removed min-max of eigenvector before performing cross-correlation showing a continuous behavior with a delay. Then ran different SSs on the same patient to see if these observations are consistent. There are different scenarios when calculating the delay such as: Maximum peak is positive or negative, The Delay of Max peak is positive or negative. Our approach is to select positive maximum peak with the positive delay. The goal is to tag or label the sources with an event (HP: M1, T1, A2, P2, LP: AO). The cross-correlation signals generated by new PCA algorithm are used as features to train the classifiers and then tag sources of a test signal. Similar approach can be extended for the identification of other cardiopulmonary signals, like coronary artery sounds, snoring, murmurs, respiration sounds in one embodiment.

Figure 9:
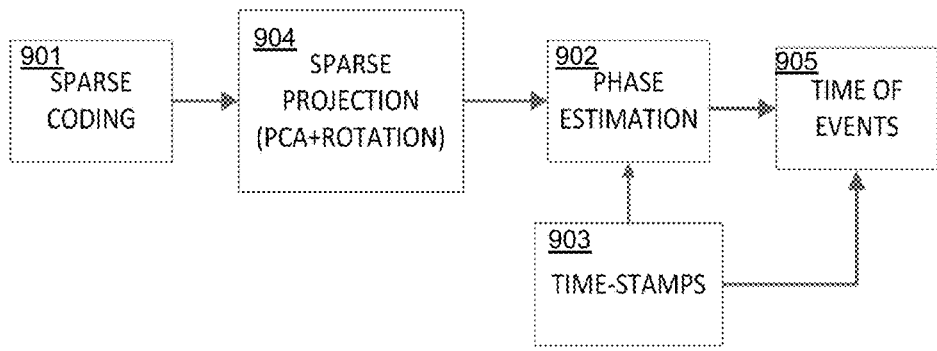
FIG. 9 is a flowchart of a method practiced by the system in accordance with an embodiment.
Figure 10:
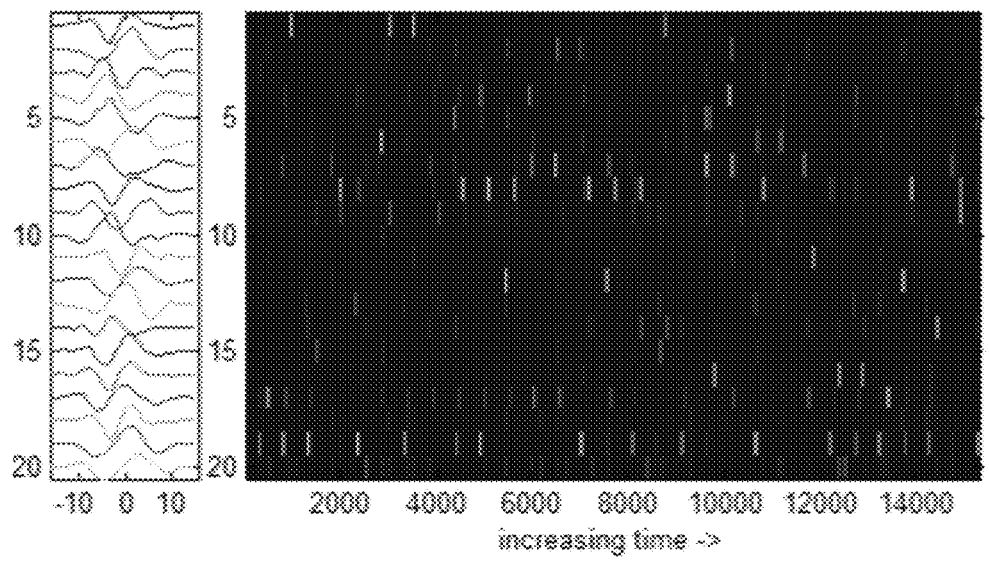
FIG. 10 is an illustration of a dictionary of signal-atoms (on a left side) and a weight matrix/loadings (on a right side) given by a sparse coding source separation algorithm in accordance with an embodiment.
Figure 11:
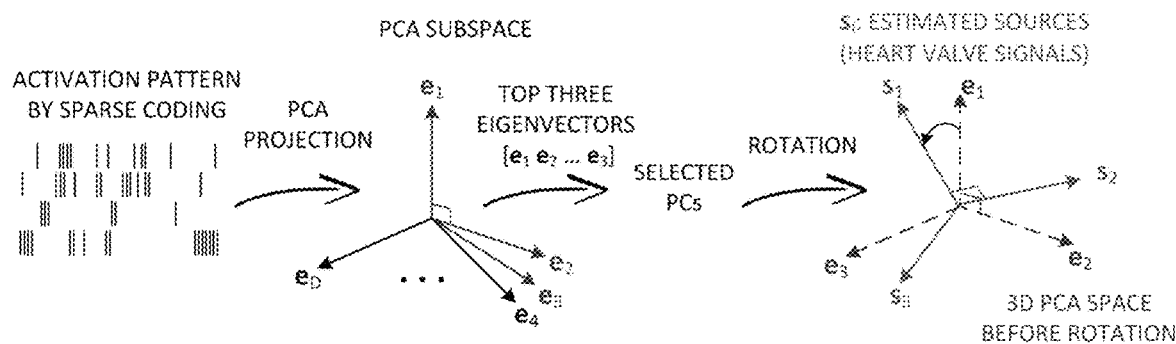
FIG. 11 is an illustration of a sparse projection of an activation pattern including PCA projection followed by subspace rotation in accordance with an embodiment.

Referring to FIGS. 9-11, The exemplary embodiments of the system and method proposed here provide a source marking algorithm for vibrations from the cardiohemic system. In some embodiments, the system includes a sparse projection of a deficient activation pattern given by an underdetermined source separation algorithm (see FIG. 9). The activation patterns (see FIG. 10) are projected to a possibly lower dimensional space of reconstructed sources. The projection consists of an unsupervised principal component analysis (PCA) metric projection, followed by a regularization step to make the projection loadings sparser. The regularization is performed by an orthogonal rotation of PCA subspace, and helps to better understand the rotated space which is now aligned with the space of valvular events (see FIG. 11).

Figure 12:
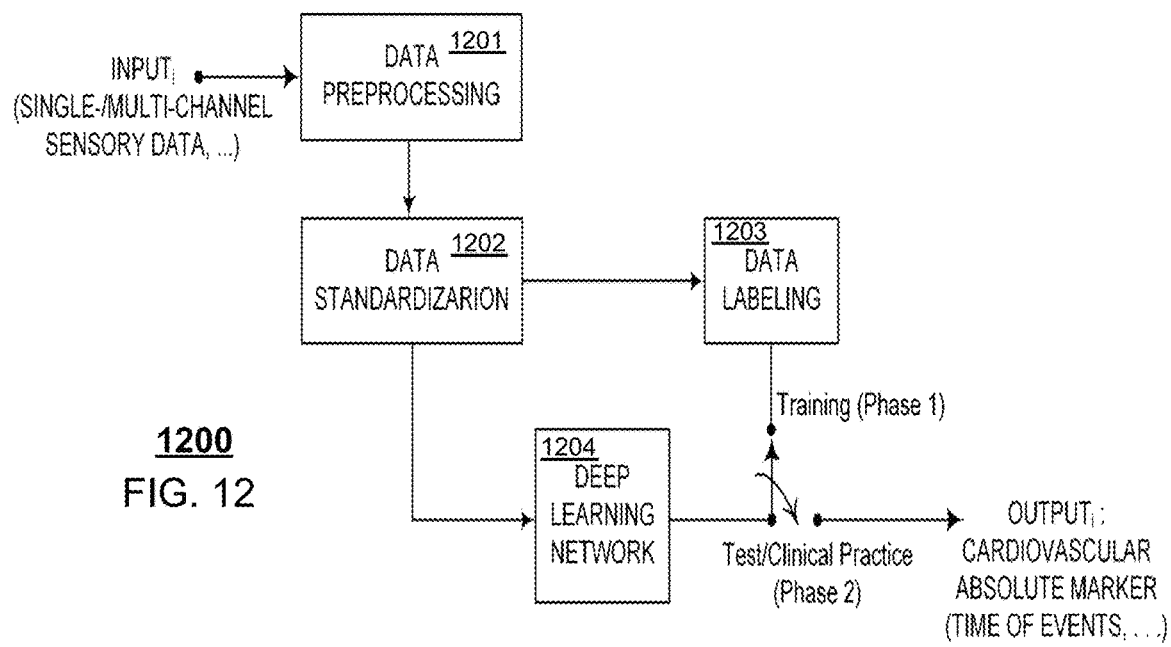
FIG. 12 is an illustration of a system based on deep learning that learns to generate cardiovascular absolute markers in accordance with an embodiment.
Figure 13:
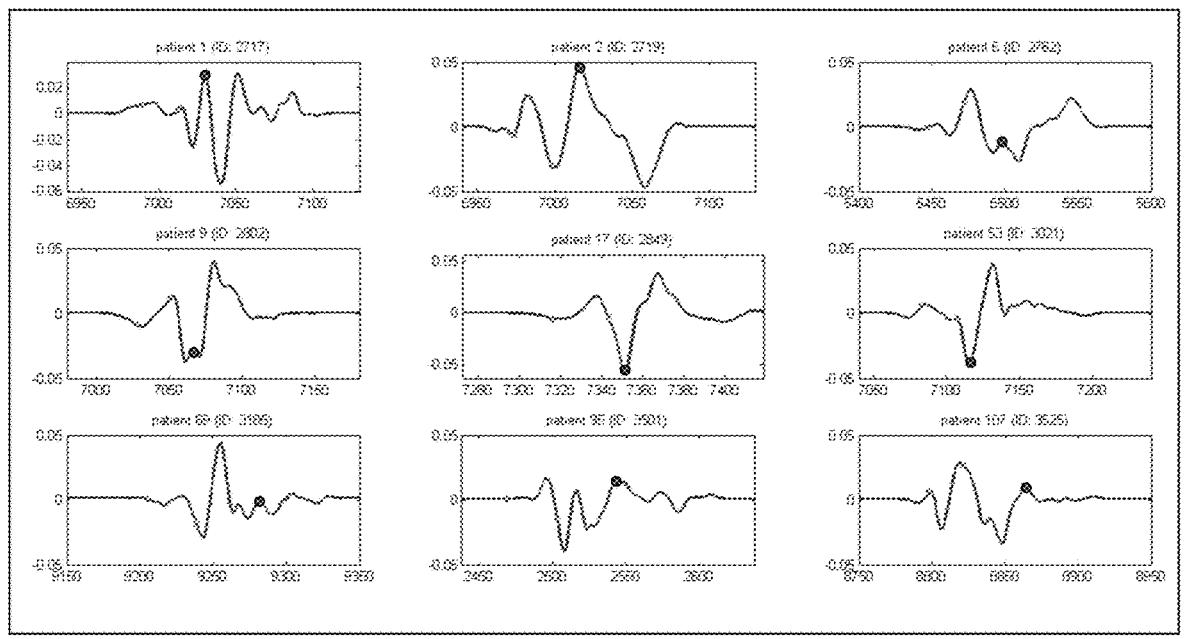
FIG. 13 is an example of data labels (pronounced dots or green stars if shown in color) for Aortic valve opening given by an automatic labeling algorithm applied to Hemotag single channel data in accordance with an embodiment.

Referring now to FIGS. 12 and 13, diagnosis of cardiovascular diseases, including heart failure, are currently based on medical experts' interpretation of patient's physical examination and medical records using a well-developed flowchart, comparing patient's conditions with a typical taxonomy of known conditions. However, this diagnostic procedure is not always accessible, and may be expensive or inefficient—as it is error-prone. An alternative approach to access appropriate medical diagnostic services is to use artificial intelligence and design rule-based expert systems or graphical models to consistently follow the same diagnostic procedure performed by a physician. However, designing a system to imitate the reasoning processes of human experts could be very challenging, as it requires significant rule extraction and feature engineering.

An alternative to artificial intelligence is deep learning that has recently produced considerable breakthroughs proven to be very efficient for image and signal analysis, like image classification and segmentation, speech recognition, language translation, and structured data analysis. Deep learning is based on deep neural networks with hierarchical intermediate layers of artificial neurons, which can progressively extract increasingly complex features. By learning very complicated input-output relationships, deep learning can outperform systems that are based on manual feature extraction, like rule-based expert systems.

A prerequisite for using deep learning is that there must be a thousand to millions of well-labeled data points (pairs of input-output) to train the deep network. With the new advances in cardiovascular technologies, which are able to capture large quantities of patients' data, this prerequisite is met. A recent survey (by Bizopoulos, P. and Koutsouris, D., 2018. Deep Learning in Cardiology. *IEEE reviews in biomedical engineering*, 12, pp. 168-193) summarizes the applications of deep learning in cardiology, where it is applied to patients' structured data, and signal and image modalities in cardiology of heart and vessel structures.

Despite of superior performance of deep learning for some cardiovascular applications, their use as a diagnostic black box prevents them to integrate in the clinical practices (as reported by Miotto, R., Wang, F., Wang, S., Jiang, X. and Dudley, J. T., 2017. Deep learning for healthcare: review, opportunities and challenges. *Briefings in bioinformatics*, 19(6), pp. 1236-1246).

We introduce a system (see FIG. 12) based on deep learning (DL) networks, which is applicable to any sensory database, image, motion image/video, single or multichannel sensor signals (from sensors such as ECG, accelerometers, gyroscopes, acoustic microphones, micro-electro-mechanical systems-MEMS, microwave, radar, radiofrequency, doppler, or Near Field Communication-NFC) and structured data and after proper training with pairs of cardiovascular input-output, can produce absolute markers, like heart valvular events (e.g., Mitral closing & opening, Tricuspid closing & opening, Aortic closing & opening, Pulmonic closing & opening), ejection fraction (EF), global longitudinal strain (GLS), left atrial volume index, different cardiac time intervals (CTI's), mean Pulmonary Artery pressures (mPAP), systolic Pulmonary Artery pressures (sPAP), and diastolic Pulmonary Artery pressures (dPAP), Pulmonary Wedge Capillary Pressure (PCWP), Cardiac Output and stroke volume. This is a totally different perspective of using deep learning, because we train the system with absolute markers so the immediate outputs of the deep learning after training are absolute markers. This is consistent with the concept of evidence-based medicine and partially satisfies the ethical and legal issues of using machine learning and artificial intelligence methods in clinical practices, which is currently a big challenge for their practical application (as discussed by Lee, E. J., Kim, Y. H., Kim, N. and Kang, D. W., 2017. Deep into the brain: artificial intelligence in stroke imaging. *Journal of stroke*, 19(3), p. 277).

The embodiment of the system and method proposed here includes a preprocessing step (noise removal, a data standardization that brings the preprocessed data to a common format (normalization, scaling, windowing, . . . ). It also includes a manual or automatic data labeling step to extract the desired outputs (labels) for each particular input (FIG. 2, shows one such embodiment of the inputs, namely, the Aortic valve openings). On training session (Phase 1) the deep learning module learns from pairs of input$_i$/output$_i$. At the end of training session the system is ready for test and clinical application (Phase 2).

The embodiment of the system and method proposed here is applicable for longitudinal monitoring of absolute markers over time, when the times series of markers provided over hours, days or weeks indicates if the patient's symptoms is improving/worsening.

The embodiment of the system and method proposed here can be used in a multidisciplinary framework to generate combined outpatient markers, like acute decompensated heart failure, heart failure with preserved ejection fraction (HFpEF) for diastolic dysfunction, heart failure with reduced ejection fraction (HFrEF) for systolic dysfunction pulmonary hypertension, different grades of diastolic dysfunction I, II, III, different grades of Mitral Valve Regurgitation (mild, moderate, moderately severe, or severe), different grades of Mitral Valve Stenosis (mild, moderate, or severe), different grades of Aortic Regurgitation (mild, moderate, moderately severe, or severe), different grades of Aortic Stenosis (mild, moderate, or severe), congestion in the lungs, Coronary Artery Disease, Lung Disease, Ischemic Cardiomyopathy, Left Ventricular Hypertrophy, Sleep Apnea, Angina, and Myocardial Infraction.

The deep learning core of the embodiment of the system and method proposed here, can be deep feed forward (DFF), deep belief network (DBN), deep convolutional network (DCN), deep convolutional inverse graphics network (DCIGN), Deep Boltzmann Machine (DBM), or any other deep structure.

It will be apparent to those skilled in the art that various modifications may be made in the present invention without departing from the spirit or scope of the invention. Thus, it is intended that the present invention cover the modifications and variations of this invention provided they come within the scope of the method and system described and their equivalents.

What is claimed is:

1. A system for marking cardiac time intervals from heart valve signals, comprising:
   one or more channels;
   a presentation device or a display;
   a non-invasive sensor unit for simultaneously capturing electrocardiogram signals and composite vibration objects of heart sounds over the one or more channels;
   a memory containing computer instructions; and
   one or more processors operatively coupled to the memory and the presentation device, an execution of the computer instructions by the one or more processors causing the one or more processors to perform operations comprising using one of:
      a first algorithm that:
         separates a plurality of individual heart vibration events from the composite vibration objects;
         defines a plurality of marking points using source separation by using a sparse coding algorithm followed by a sparse projection that includes a principal component analysis and an orthogonal rotation of a PCA subspace;
         marks cardiac time intervals by measuring the time of an occurrence of the individual heart vibration event defining the plurality of marking points for the occurrence at a start and an end of each of the heart vibration events; or
      a second algorithm that:
         defines a plurality of marking points using a deep learning algorithm trained with absolute markers so that immediate outputs provide absolute markers of heart valvular events;
         marks cardiac time intervals by measuring the time of an occurrence of the individual heart vibration event defining the plurality of marking points for the occurrence at a start and an end of each of the heart vibration events; and
   wherein the one or more processors uses an output from the first algorithm or the second algorithm to present at least the marking points and the respective cardiac time intervals via the display or the presentation device and wherein the output provides an indication of a cardiovascular disease when present from individual vibration objects from cardiac vibration objects and pulmonary vibration objects.

2. The system of claim 1, wherein the one or more processors perform the functions of the second algorithm using:
   a data pre-processing unit for noise removal;
   a data standardization unit coupled to the data pre-processing unit; and
   a deep learning network unit coupled to the data standardization unit, wherein the deep learning network unit is configured to:
      learn from pairs of inputs and outputs during a training session during a first phase and test and perform clinical applications at the end of the training session during a second phase;
      perform longitudinal monitoring of the absolute markers or of the absolute markers over time when a time series of markers provided over a predetermined time frame indicates symptoms that are improving or worsening.

3. The system of claim 2, wherein the deep learning network unit operates on the electrocardiogram signals and the heart sounds simultaneously.

4. The system of claim 2, wherein the data standardization unit brings pre-processed data from the data pre-processing unit to a common format using normalization, scaling, and windowing and the system further comprises a data labeling unit that extracts desired output or labels for each input.

5. The system of claim 2, further comprising a multidisciplinary framework of the deep learning network, wherein the deep learning network generates combined outpatient markers, among acute decompensated heart failure, heart failure with preserved ejection fraction (HFpEF) for diastolic dysfunction, heart failure with reduced ejection fraction (HFrEF) for systolic dysfunction pulmonary hypertension, different grades of diastolic dysfunction I, II, III, different grades of Mitral Valve Regurgitation (mild, moderate, moderately severe, or severe), different grades of Mitral Valve Stenosis (mild, moderate, or severe), different grades of Aortic Regurgitation (mild, moderate, moderately severe, or severe), different grades of Aortic Stenosis (mild, moderate, or severe), congestion in the lungs, Coronary Artery Disease, Lung Disease, Ischemic Cardiomyopathy, Left Ventricular Hypertrophy, Sleep Apnea, Angina, and Myocardial Infraction.

6. The system The system of claim 2, wherein the deep learning network unit uses one of a deep feed forward (DFF), deep belief network (DBN), deep convolutional network (DCN), deep convolutional inverse graphics network (DCIGN), and Deep Boltzmann Machine (DBM).

7. The system of claim 1, wherein the one or more processors determine the indication of the cardiovascular disease from individual vibration objects from the cardiac vibration objects and the pulmonary vibration objects.

8. The system of claim 1, wherein the non-invasive sensor unit is configured to capture the electrocardiogram signals and the composite vibration objects at different locations simultaneously and wherein the one or more processors determines the indication of the cardiovascular disease from the individual vibration objects from the cardiac vibration objects and the pulmonary vibration objects.

9. The system of claim 1, wherein the non-invasive sensor unit is configured to capture the electrocardiogram signals and the composite vibrations objects over the one or more channels to provide spectral information, relationships among the one or more channels, and relationships among the individual heart vibration events in terms of relative times of occurrence.

10. The system of claim 1, wherein the non-invasive sensor unit when using the first algorithm comprises at least one or more sensors using a tri-axial accelerometer configured for placement on different points of a body and wherein each of separated sources resulting from the separating of the plurality of individual heart vibration events from the composite vibrations events results from events among one or more of valve murmurs, heart wall motions, coronary artery sounds, valve sounds of a mitral valve closing, a mitral valve opening, a tricuspid valve closing, a tricuspid valve opening, an aortic valve closing, an aortic valve opening, a pulmonic valve closing, and a pulmonic valve opening, pulmonary vibration events of respiratory lung sounds, breathing sounds, tracheobronchial sounds, vesicular sounds, broncho vesicular sounds, and snoring sounds.

11. The system of claim 1, wherein the system when using the first algorithm marks cardiac time intervals by further measuring cumulative energy within the individual heart vibration event, processing the cumulative energy within the individual heart vibration event, and setting an energy threshold that defines the marking point for the occurrence of each of the heart vibration events.

12. The system for measuring cardiac time intervals of claim 1, wherein when using the first algorithm, the one or more processors perform the source separation of the composite vibration objects to provide source separated signals and wherein a number of vibration sensors in the non-invasive sensor unit which includes two or more vibration sensors is less than a number of sources for the source separated signals where the number of sources includes three or more sources.

13. The system of claim 1, wherein when using the first algorithm, the one or more processors use at least one among the Principal Component Analysis (PCA), machine learning, Singular Value Decomposition (SVD), k nearest neighbors, Linear LDA, Quadratic LDA, or Support Vector Machine (SVM), to find timing information for the individual heart vibration events and delay between the one or more channels and to determine which source is associated with which heart valve signal.

14. The system of claim 1, wherein the marking of cardiac time intervals comprises at least the marking of one or more among a Mitral valve opening (MO), Aortic valve opening (AO), Tricuspid valve opening (TO), Pulmonary valve opening (PO), a third sound, a fourth sound, murmurs, heart wall motions, a coronary artery sound, pulmonary vibration objects, a bronchovesicular sound, or cardiac time intervals within a uterus.

15. A system for marking cardiac time intervals from heart valve signals, comprising:
one or more channels;
a presentation device or a display;
a non-invasive sensor unit for capturing electrocardiogram signals and composite vibration objects of heart sounds over the one or more channels;
a memory containing computer instructions; and
one or more processors using a deep learning algorithm inputting the electrocardiogram signals and the composite vibration objects of heart sounds over the one or more channels and operatively coupled to the memory and the presentation device or the display, an execution of the computer instructions by the one or more processors causing the one or more processors to perform operations comprising:
marking cardiac time intervals by measuring the time of occurrence of individual heart vibration events defining marking points for the occurrence of a start and end of each of the heart vibration events wherein defining the marking points is done using a deep learning algorithm trained with absolute markers so that immediate outputs of the deep learning after training are absolute markers of heart valvular events; and
wherein the one or more processors present at least the marking points and the respective cardiac time intervals via the display or the presentation device providing an indication of a cardiovascular disease if present.

16. A system for marking cardiac time intervals from heart valve signals, comprising:
one or more channels;
a presentation device or a display;
a non-invasive sensor unit for capturing electrocardiogram signals and composite vibration objects over the one or more channels;
a memory containing computer instructions; and
one or more processors operatively coupled to the memory and the presentation device or the display, an execution of the computer instructions by the one or more processors causing the one or more processors to perform operations comprising:
separating a plurality of individual heart vibration events from the composite vibration objects;
defining a plurality of marking points using source separation by using a sparse coding algorithm followed by a sparse projection that includes a principal component analysis and an orthogonal rotation of a PCA subspace;
marking cardiac time intervals by measuring the time of an occurrence at a start and an end of each of the individual heart vibration events defining a marking point for the occurrence of a start and end of each of the heart vibration events; and
wherein the one or more processors uses an output that defines the plurality of marking points to present at least the marking points and the respective cardiac time intervals via the display or the presentation device and wherein the output provides an indication of a cardiovascular disease when present from individual vibration objects from cardiac vibration objects and pulmonary vibration objects.

* * * * *